United States Patent [19]
George

[11] Patent Number: 5,865,772
[45] Date of Patent: Feb. 2, 1999

[54] INTRINSIC PUMP FOR VACCUM SEALING CAST PROTECTORS

[76] Inventor: Frederick W. George, 117 Memorial Ave., Christchurch, New Zealand

[21] Appl. No.: 843,913

[22] Filed: Apr. 17, 1997

[51] Int. Cl.$^6$ .............................. A61F 5/00; A61F 13/00
[52] U.S. Cl. .................................... 602/3; 602/5; 602/60
[58] Field of Search .............................. 602/3, 5, 13, 60, 602/62; 128/DIG. 20; 222/209, 401

[56] References Cited

U.S. PATENT DOCUMENTS

| | | | |
|---|---|---|---|
| 2,795,245 | 6/1957 | Meehan | 222/209 X |
| 3,741,203 | 6/1973 | Liman | 602/3 |
| 3,785,374 | 1/1974 | Lipson | 602/3 |
| 4,098,268 | 7/1978 | Scott | 602/3 |
| 4,657,003 | 4/1987 | Wirtz | 128/133 |
| 4,768,501 | 9/1988 | George | 128/82 |
| 5,139,475 | 8/1992 | Robicsek | 602/13 X |
| 5,218,954 | 6/1993 | van Bemmelen | 128/24 |
| 5,405,671 | 4/1995 | Kawin et al. | 602/3 |
| 5,728,052 | 3/1998 | Meehan | 602/3 |

*Primary Examiner*—Richard J. Apley
*Assistant Examiner*—Denise Pothier
*Attorney, Agent, or Firm*—Flehr Hohbach Test Albritton & Herbert LLP

[57] ABSTRACT

Method and apparatus in which a pump is used with a sanative protector of the type having a flexible envelope which wraps around and seals a cast, bandage or dressing on an arm, leg or other appendage of a person responsive to vacuum established in an interface region beneath the envelope. The pump comprises a bulb having a wall which encloses a pumping chamber. The wall is formed of a material and wall thickness which provides elasticity sufficient to enable inward deformation from a distended shape toward a collapsed shape, and further having an elastic memory which causes the wall to produce an elastic pressure sufficient to urge the wall outwardly from the collapsed shape toward the distended shape. A flow control mechanism enables fluid flow from within the interface region through an inlet in the bulb into the pumping chamber for reducing the vacuum level as the bulb expands toward its distended shape, and the mechanism further establishes a second path for discharging fluid from the pumping chamber to ambient atmosphere when the bulb is squeezed toward its collapsed shape.

5 Claims, 2 Drawing Sheets

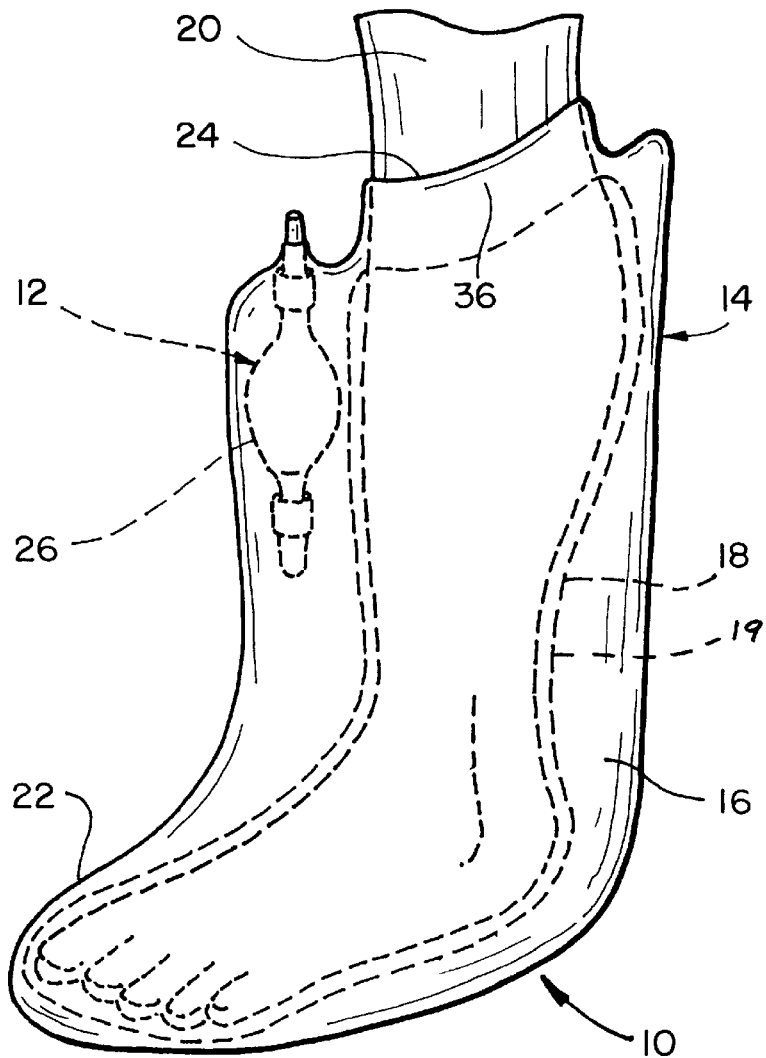
FIG_1
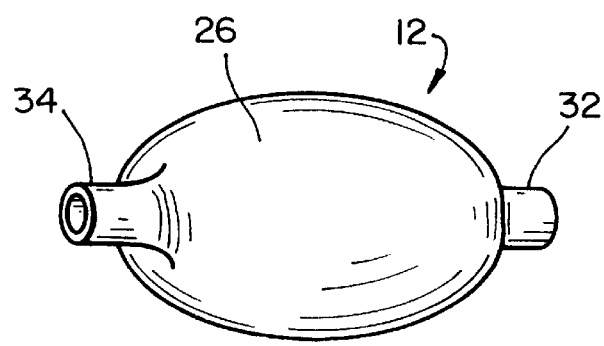
FIG_3

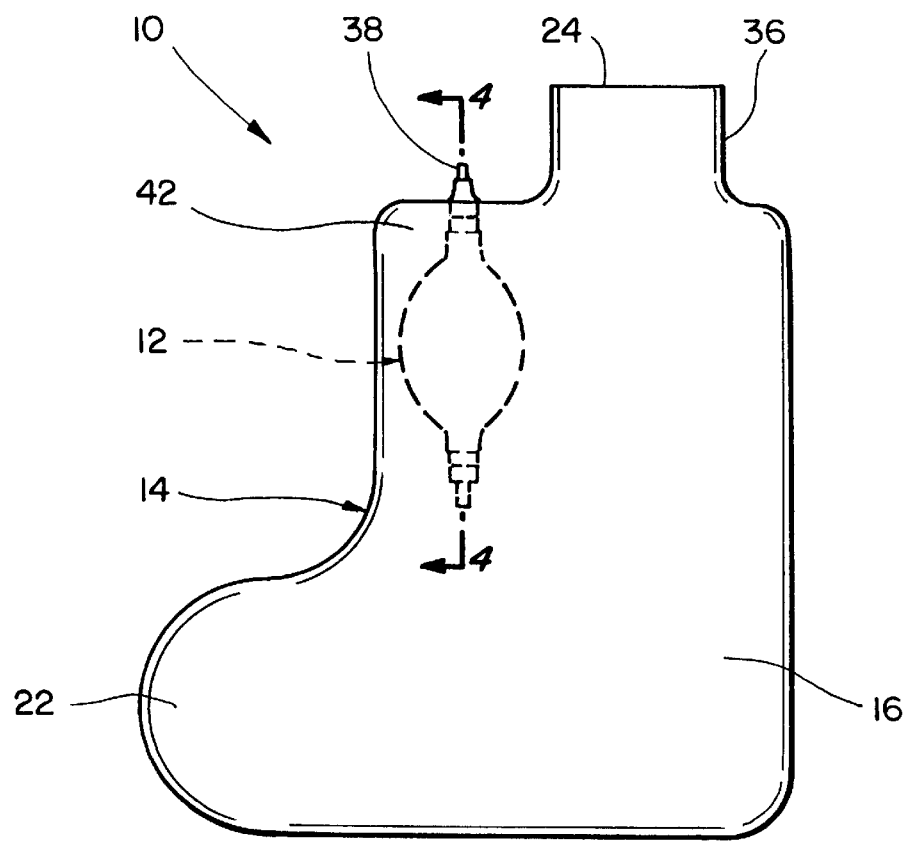
FIG_2
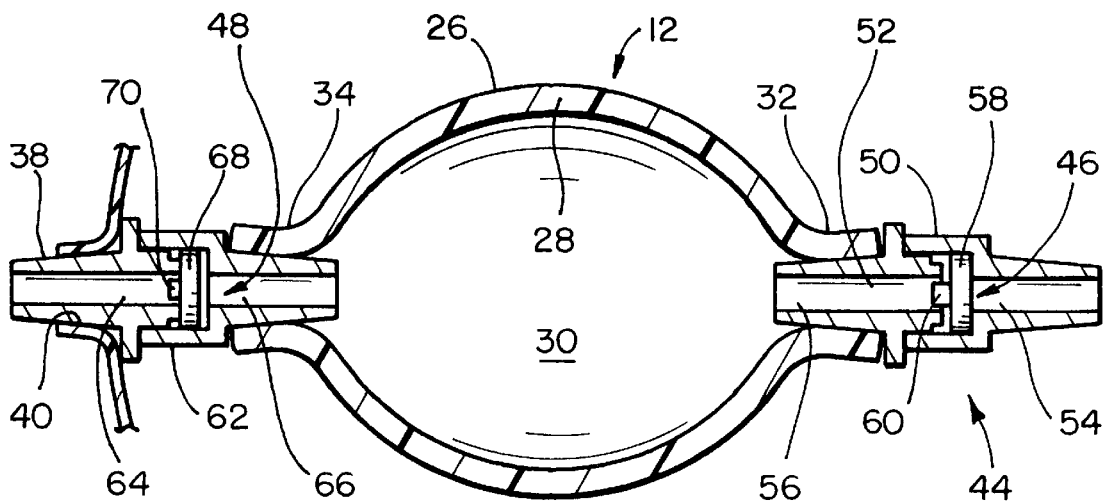
FIG_4

INTRINSIC PUMP FOR VACCUM SEALING CAST PROTECTORS

BACKGROUND OF THE INVENTION

1. Field of the Invention

This invention relates in general to sanative protective coverings in the medical field, and in particular relates to vacuum sealing protectors for covering casts, bandages and other dressings on a patient.

2. Description of the Related Art

U.S. Pat. No. 4,768,501 for Method of Waterproof Sealing of Casts and Dressings, issued to the inventor of the present invention, discloses and claims methods for the waterproof sealing of a cast or dressing on a patient using a water-and-air-impervious flexible membrane by creating a vacuum beneath the portion of the membrane which overlies the cast or dressing as well as portions of the patient's skin lying along the perimeter edge of the cast or dressing. The vacuum is established either through the use of a tube having one end inserted through the interface between the membrane and skin with the other end connected to a vacuum source, or in another embodiment through an air valve in the membrane which is connected to the vacuum source.

In the prior art sanative protectors of the type described oral evacuation of air from the interface region beneath the membrane has been used by the patient or health care professional sucking air through the distal end of the tube. While this method has the advantage of simplicity, some patients feel squeamish about inhaling air from their injured area, especially after some weeks without bathing it. In addition, the inhalation of air through a vinyl hose from a rubber sanative protector is of questionable sterility from the beginning, and this is especially so after the cast or dressing protector has been in use for several weeks.

There is a growing market for the sanative protector in hospital care, rest home care, home care and physical therapy where the person applying and evacuating the sanative protector is not the patient but rather is a health care professional or other person. In these cases the person would find it undesirable to inhale air from the patient's injured area, especially if the injury, rather than being a simple fracture in a cast, has a sepsis problem. For example, the injury could be an open, infected ulcer, or the sanative protector could be covering the lower abdomen and inguinal area. Also, under these conditions even the patient should not inhale air from an infected area directly into the lungs. Therefore, for antiseptic reasons, these prior art methods for creating the vacuum in such a sanative protector are undesirable. Another disadvantage from these prior art methods is that the health care provider oftentimes cannot expend the effort of going from patient to patient for repeatedly evacuating such a sanative protector. Where the users are infirm or geriatric patients, they often are so weak they cannot expend the effort of inhaling to evacuate the sanative protectors.

In the prior art sanative protectors it is difficult to operate the vacuum source to achieve a consistent "target" level of vacuum which is adequate to maintain the waterproof seal about the protector and without being excessive and unsafe. The need has therefore been recognized for a sanative protector of the type described which obviates the foregoing and other limitations and disadvantages of the prior art sanative protectors. There has heretofore not been provided a suitable and attractive solution to these problems.

OBJECTS AND SUMMARY OF THE INVENTION

It is a general object of the present invention to provide a new and improved vacuum pump for a sanative protector of the type employing a flexible envelope which wraps around and seals a cast, bandage or dressing where a vacuum is established in an interface region beneath the envelope.

Another object is to provide a new and improved method for producing a vacuum in a sanative protector of the type which employs a flexible envelope which wraps around and seals a cast, bandage or dressing where a vacuum is established in an interface region beneath the envelope.

Another object is to provide a method for indicating either a normal or abnormal level of vacuum relative to a target vacuum level in a sanative protector of the type which employs a flexible envelope which wraps around and seals a cast, bandage or dressing where a vacuum is established in an interface region beneath the envelope.

The invention in summary comprises a pump and method of operation for a vacuum-sealing sanative protector for use with medical casts, bandages or dressings. The pump comprises a bulb having an elastic wall which encloses a pumping chamber. The pumping chamber is connected by a flow control mechanism for pumping air out of the interface region between the envelope of the protector and the underlying portions of the cast, bandage or dressing. The elasticity of the pump wall is sufficient to enable it to deform from a distended shape toward a collapsed shape when inward pressure is applied to the bulb as by manually squeezing it. This pumps air from the chamber through the flow control mechanism outwardly to ambient atmosphere. The wall has an elastic memory which produces an elastic pressure that is sufficient to urge the wall to expand outwardly toward its distended shape for pumping air from the interface region through the flow control mechanism into the pumping chamber. In the method the shape of the wall can be detected as being either collapsed for indicating a normal level of target vacuum within the interface region or as distended for indicating an abnormal level of the vacuum. The flow control mechanism includes check valves having valve members which are mounted to freely float between open and closed positions responsive to forces produced by the flow of fluid acting on the valve members.

The foregoing and additional objects and features of the invention will appear from the following specification in which the several embodiments have been described in conjunction with the accompanying drawings.

BRIEF DESCRIPTION OF THE DRAWINGS

FIG. 1 is a perspective view illustrating a pump in combination with a sanative protector in accordance with one embodiment of the invention shown in use on the leg cast of an injured person.

FIG. 2 is a schematic side elevational view illustrating the combination pump and sanative protector of FIG. 1.

FIG. 3 is a perspective to an enlarged scale illustrating the bulb which forms a part of the combination shown in FIGS. 1 and 2.

FIG. 4 is a longitudinal section view to an enlarged scale taken along the line 4—4 of FIG. 2.

DESCRIPTION OF THE PREFERRED EMBODIMENTS

In the drawings, FIGS. 1 and 2 illustrate generally at 10 a combination pump 12 and sanative protector 14 in accordance with one preferred embodiment of the invention.

Sanative protector 14 can advantageously be made in accordance with the disclosure of U.S. Pat. No. 4,768,501, the disclosure of which is incorporated herein by this reference. Protector 14 is comprised of a flexible envelope 16, preferably formed of a water- and air-impervious flexible membrane, of a size and shape suitable for covering the desired cast, bandage or dressing on the arm, leg or other appendage of a person. FIG. 1 shows the protector in use on a typical foot-lower leg cast 18. The envelope can be fabricated from a suitable elastomer, such as any of the natural or synthetic elastomers disclosed in U.S. Pat. No. 4,768,501. The film thickness can be varied depending upon the type of material employed, also as described in that patent. In the illustrated embodiment which is shown for use in protecting a cast on a person's foot and lower leg 20, the envelope comprises a tubular sheath having a closed distal end 22 and an open proximal end 24. Also in this embodiment the material which forms the envelope portion overlying pump 12 can be visually observed by the patient or health care provider, as explained more fully below. As desired, the portion of the envelope covering one or both sides of the pump could be translucent with all or a part of the remaining envelope portions opaque such as by covering those portions with a coating of opaque paint or the like.

Pump 12 is comprised of a resilient squeeze bulb 26 in the shape of a hollow oblate spheroid having a generally elliptical longitudinal section and circular cross section as shown in FIGS. 3 and 4. The bulb has an outer wall 28 enclosing a pumping chamber 30, with the opposite ends of the wall merging into respective inlet end 32 and outlet end 34 which are generally tubular in shape.

As disclosed in U.S. Pat. No. 4,768,501, when air is withdrawn from beneath the envelope a vacuum is formed at the interface between the envelope and the outer surface of the cast (or bandage or dressing as the case may be) as well over the portions of the user's skin along the opening which penetrates through the envelope. In the illustrated embodiment the cuff portion 36 of the protector (FIG. 1) which extends above the top of the cast overlies and encircles an annular band of skin about the user's calf. This establishes an interface region beneath the envelope from which air is withdrawn by the action of pump 12 to create a vacuum. The atmospheric pressure on the area of the envelope over the vacuum in the interface region forces the envelope into hermetical sealing contact with the skin and also into a snug, close fit with the cast as well as the outer surface of bulb 12.

Bulb outlet end 34 is mounted by a ferrule 38 through a small opening 40 formed in a perimeter portion 42 near the top of the envelope. The portion of the envelope around the opening is adhered to the outer surface of the ferrule to provide an hermetical seal. In the illustrated application for use on the user's leg and/or foot, the bulb preferably is mounted near the top of the envelope for enabling the user to conveniently reach and operate the bulb.

Flow control mechanism 44 is provided for establishing a first path for the flow of fluid, which in the illustrated embodiment is air, from within the interface region through bulb inlet end 32 into pumping chamber 30 while blocking flow of fluid through the bulb outlet 34 into the pumping chamber. This mechanism comprises an inlet check valve 46 which is mounted within the tubular inner surface of inlet end 32 and an outlet check valve 48 which is mounted within the tubular inner surface of outlet end 34. FIG. 4 shows details of the construction of inlet check valve 46 which is comprised of a cylindrical body 50 having a cavity 52 that is exposed through opening 54 to the interface region beneath the envelope. This opening 54 forms a valve seat. The cavity is also exposed to the pumping chamber through an opening 56 formed at the opposite end of the body. A disk-shaped valve member 58 is mounted to float, responsive to fluid pressure, for axial movement within the cavity between an open position axially spaced from the valve seat (to the left in FIG. 4) and a closed position in occluding relationship against the valve seat formed by opening 54. The limit of travel of the valve member in its open position is determined by a stop member 60 which is mounted on the inside of the cavity. With the valve member moved away from its closed position, air is enabled to flow along the first path from the interface region through the opening forming the valve seat, thence along the outer perimeter of the valve member, thence along the length of cavity 52 and thence through opening 56 and into the pumping chamber. This mode of operation of the valve member is responsive to outward expansion of bulb wall from a collapsed shape toward the distended shape shown in FIGS. 3 and 4. This outward expansion lowers the internal pressure within the pumping chamber which initially begins suctioning air into both ends of the bulb. The initial flow of air through outlet end 34 closes outlet check valve 48 in the manner described below so that further expansion of the wall continues to withdraw air from the interface region through the open inlet check valve 46 until the elastic pressure forces acting on the bulb are equalized, also in the manner explained below.

FIG. 4 illustrates details of outlet check valve 48. This check valve is similar in construction to the inlet check valve, and comprises a cylindrical body 62 having a cavity 64 which forms a part of the second path for the flow of air from the pumping chamber through the bulb outlet. The body is formed with an opening 66 which is the valve seat. A valve member 68 is mounted within the cavity for axial floating movement responsive to the fluid. The valve member in its closed position is moved into occluding relationship with opening 66, and in its open position the valve member is axially spaced from the opening (to the left in FIG. 4). A stop 70 mounted in the cavity limits the extent of movement of the valve member in its open position. When bulb wall 28 expands toward its distended shape so as to reduce air pressure within the pumping chamber, air initially begins inward movement through the cavity, thus moving outlet valve member 68 to its closed position, and it remains in this position until air pressure in the pumping chamber again exceeds ambient air pressure.

When the user squeezes the bulb the applied pressure on wall 28 deforms it from the distended shape toward a collapsed shape. This increases air pressure within the pumping chamber so that air begins to flow outwardly from the chamber 30 through both the inlet and discharge ends. The initial flow of air through the inlet end 32 forces actuating member 58 to its closed position against the valve seat, and at the same time the flow of air through the outlet end moves valve member 68 into its open position. This establishes a second path for the flow of air from the pumping chamber through the bulb outlet for discharge outside the envelope and into ambient atmosphere.

The bulb wall material and thickness are selected so that the wall has an elasticity which is sufficient to deform responsive to an applied pressure from a distended shape toward a collapsed shape, and which also has sufficient elastic memory to exert an outwardly directed restoring force that produces an elastic pressure sufficient to expand the wall outwardly from the collapsed shape toward the distended shape. As used herein, the term "applied pressure" means the force per unit area applied manually, as by squeezing, or mechanically on the outer surface of the bulb to cause the wall to deform toward the collapsed shape. Also as used herein, the term "elastic pressure" means the elastic restoring force per unit area on the wall produced by elastic memory in the material of the wall which urges the wall to expand outwardly. The terms "vacuum pressure" or "vacuum level" mean the absolute pressure so that the term "increase in vacuum level" means a decrease in the absolute pressure within either the pumping chamber or the interface region 19, while the term "decrease in vacuum level" means an increase in the absolute pressure. The term "interface region" means the space or region and the cast, between the envelope and bandage or dressing and the adjacent portion of the user's skin with which the overlying portion of the envelope creates an hermetical seal when a vacuum is created beneath the envelope.

The nature of the bulb wall material and the wall's thickness, taken with the overall size and configuration of the bulb, are selected so that the wall's properties are in accordance with the following formulae:

$$EP(bulb) > AtmP - VacP(pumping\ chamber) \quad \text{(Equation 1)}$$

where EP(bulb) is the elastic pressure in the bulb wall resulting from its elastic memory, and AtmP is the atmospheric pressure, and VacP(pumping chamber) is the absolute pressure of vacuum in the pumping chamber. Equation 1 gives the relationship of pressure when the bulb expands outwardly from the collapsed shape.

$$P(applied) + AtmP > EP(bulb) + VacP(pumping\ chamber) \quad \text{(Equation 2)}$$

where P(applied) is the applied pressure on the bulb wall resulting from manually squeezing it. Equation 2 gives the relationship of pressure when the bulb is squeezed and deforms inwardly from the distended shape.

In each pumping cycle the squeeze phase discharges air within the pumping chamber to the atmosphere while flow is blocked into the bulb inlet. During the release phase the bulb inlet is opened so that $$VacP(target) = VacP(pumping\ chamber) \quad \text{(Equation 3)}$$

where VacP(target) is the desired level of vacuum within the interface region which is determined to be adequate to maintain the waterproof seal for the cast, bandage or dressing resulting from atmospheric pressure in squeezing the flexible envelope over the underlying areas of the user's skin as well as the cast, bandage or dressing. Preferably the target vacuum is in the range of 90 mm Hg to 380 mm Hg.

The bulb is squeezed a sufficient number of times to bring the pressure level within the interface region down to the preselected target vacuum, which condition occurs when $$EP(bulb) = AtmP - VacP(target) \quad \text{(Equation 4)}$$

When the pressure balance of Equation 4 exists then the bulb normally stays in its collapsed shape at the target vacuum level, which exists both in the pumping chamber and the interface region. The user can readily determine when the target vacuum is reached by observing when the bulb does not return to its distended shape after being squeezed. The bulb inherently provides a safety factor in that when it remains collapsed at the target vacuum condition then it is not possible to continue the pumping action. Thus the problem of inadvertently increasing the vacuum level to an unsafe condition is obviated. In addition, the user does not have to guess as to when a sufficient vacuum level is achieved for the waterproof seal since he or she cannot continue squeezing the bulb when it collapses. When the target vacuum level is reached then the pump physically stops working.

The invention provides a simple methodology for the user or health care provider to readily determine the existence of either a normal or abnormal level of vacuum in the interface region relative to the target vacuum. The normal condition is when the target level is reached, and in this case the flexible envelope is "snugged down" by atmospheric pressure over the collapsed squeeze bulb. This enables the user to either tactilely feel the bulb to determine its shape, or detect the shape by visual observation of the snugged down portion of the envelope over the bulb. In addition, the envelope could be made of translucent material over the bulb to enhance observation of it.

In the flattened shape the elastic memory of the bulb wall maintains a steady force, per Equation 4, in balance with the difference between atmospheric pressure and the level of vacuum within the pumping chamber and interface region. This obviates the problem of air leakage into outlet check valve 48 by constantly maintaining VacP(pumping chamber) less than AtmP such that the differential in pressure on floating valve member 68 establishes a constant force pulling it against valve seat 66. This function would not be performed by envelope 16 alone because the flexibility of its thin-walled construction would not maintain the essential steady suction force. This aspect of the invention in maintaining a steady force holding the outlet valve closed is important because any leakage, of either air or water entering through the outlet valve, would cause vacuum to be lost inside the sanative protector which in turn would cause the seal around the user's skin to be lost. The protector's envelope would then become baggy and thereby not serve its intended purpose.

To provide the above-described properties for the bulb, the wall material and wall thickness can be selected in accordance with the desired target vacuum. The wall thickness can vary in the range of $\frac{1}{8}$" to $\frac{1}{4}$", and the wall material can be a suitable natural or synthetic elastomer having a Young's modulus of elasticity comparable to that of natural latex rubber. A material suitable for this purpose includes raw latex natural rubber obtained from Guthrie Latex USA which is fabricated into the squeeze bulb of the invention in the following formulation: raw latex; potassium hydroxide; surfactant; sulfur; heptene base; Methyl Zimate, a brand product of R. F. Vanderbilt; zinc oxide; calcium carbonate; titanium dioxide; and color pigment. The Young's modulus of elasticity for the resulting squeeze bulb is 1200 psi at 300% elongation. The tensile strength is 3000 psi minimum, and the percent elongation is 700% minimum (at failure). Other wall materials can be selected with varying elastic properties to provide the desired target vacuum, and the wall thickness can also be varied in accordance with the desired target vacuum.

An example of the invention is the use of natural latex rubber having an elasticity which, in combination with a wall thickness of $\frac{1}{4}$", produces an elastic pressure EP(bulb) of 460 mm Hg (8.878 lb/in$^2$). Assuming that atmospheric pressure is 760 mm Hg, then using Equation 4 the target vacuum VacP(target) would be 300 mm Hg. Therefore at the start of a pumping cycle the amount of applied pressure to begin squeezing the bulb 25 shown from Equation 2 must be greater than 460 mm Hg (8.878 lb/in$^2$). Assuming that after a few squeezes of the bulb there is an increase in the vacuum level of the pumping chamber to, for example, 500 mm Hg, then Equation 1 shows that the amount of the restoring pressure which distends the bulb from its collapsed shape would be equal to 460 mm Hg−(760 mm Hg−500 mm Hg)=200 mm Hg (3.86 lb/in$^2$). When this vacuum level further increases to the 300 mm Hg target level then, in accordance with Equation 4, there is no longer a pressure differential in that the bulb's elastic pressure equals the atmospheric pressure less the vacuum level in the pumping chamber so that the bulb remains in its collapsed shape.

From the foregoing it is apparent that applicant has provided a new and improved combination pump and vacuum sealing sanative protector. The pump can be easily operated by the user or health care professional merely repeatedly squeezing the bulb. The pump permits the level of vacuum to be raised only to the predetermined consistent target level which is adequate to maintain the waterproof seal in the protector without the vacuum being excessive and unsafe. The pump automatically stops working and remains in a flattened shape when the target vacuum is attained, which is the normal condition. The shape of the bulb can be detected either tactilely or visually to provide an indication of either a normal or abnormal level of vacuum relative to the target vacuum. The pump maintains a steady suction force when flattened in the normal stage, thereby preventing the outlet check valve from leaking which in turn obviates the problem of losing vacuum within the protector.

As a result of the intrinsic design in which the pump is mounted within the envelope of the protector, when under vacuum, the envelope "snugs down" on the pump, holding it firmly in place. This enables the user to engage in activities such as swimming, or walking on a submerged treadmill in water therapy, without the pump moving about and interfering with the activity. The pump is also protected from damage or from being torn away by being snagged on other objects. The intrinsic mounting of the pump also obviates the problem of it being lost or mislaid as in the case of a detachable pump.

The pump of the invention also enables it to be operated completely by one hand of the user. This is a necessity in the case where the sanative protector is used on one of the upper extremities, such an arm or hand. In such case the other arm and hand would be available to operate the pump to create the vacuum. The invention provides a single-patient-use disposable sanative protector with the pump being intrinsically mounted. This prevents any cross-contamination of infection from patient to patient. The design of the combination pump and sanative protector is such that it may be economically disposed of.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. A combination intrinsic pump and sanative protector for use with medical casts, bandages or dressings comprising a flexible waterproof envelope of a size which is sufficient to wrap around the cast, bandage or dressing, a pump carried by the envelope, the pump comprising a bulb having an inlet and an outlet, the bulb further having a wall which encloses a pumping chamber, the wall having an elasticity which is sufficient to enable inward deformation of the wall from a distended shape toward a collapsed shape responsive to an applied pressure from forces that are directed inwardly against the wall, said wall further having an elastic memory which causes the wall to exert outwardly directed forces that produce an elastic pressure which is sufficient to urge the wall to expand outwardly from the collapsed shape toward the distended shape, and a flow control mechanism for establishing a first path for the flow of fluid from within the interface region through the bulb inlet into the pumping chamber while blocking flow of fluid through the bulb outlet into the pumping chamber responsive to said expansion of the wall toward the distended shape, the flow control mechanism further establishing a second path for the flow of fluid from the pumping chamber through the bulb outlet for discharge outside of the envelope responsive to said deformation of the wall toward the collapsed shape while blocking said flow of fluid through the bulb inlet into the pumping chamber.

2. A combination intrinsic pump and sanative protector as in claim 1 in which the bulb is mounted within said interface region.

3. A combination intrinsic pump and sanative protector as in claim 1 in which said elastic memory is sufficient to cause the elastic pressure exerted by the bulb wall to be equal to the difference between the pressure of one atmosphere and a preselected target vacuum pressure to be maintained within the interface region.

4. A combination intrinsic pump and sanative protector as in claim 1 in which the flow control mechanism comprises an outlet check valve mounted in the outlet, the outlet check valve comprises a body having a cavity which forms a part of the second path, a valve seat in the pumping chamber and a valve member which is mounted for movement between an open position and a closed position, said valve member in the open position being spaced from the valve seat a sufficient distance for enabling the fluid to flow along the second path from the pumping chamber through the valve seat and through the bulb outlet.

5. A pump as in claim 4 in which the valve member is mounted to float between the open and closed positions responsive to forces produced by the fluid acting on the valve member.

* * * * *